(12) United States Patent
Saul et al.

(10) Patent No.: US 7,410,808 B1
(45) Date of Patent: Aug. 12, 2008

(54) METHOD AND ASSAY FOR DETECTION OF RESIDUES

(75) Inventors: Steven J. Saul, Arlington, MA (US); Robert J. Markovsky, Brentwood, NH (US); David W. Douglas, Andover, MA (US)

(73) Assignee: Charm Sciences, Inc., Lawrence, MA (US)

( * ) Notice: Subject to any disclaimer, the term of this patent is extended or adjusted under 35 U.S.C. 154(b) by 385 days.

(21) Appl. No.: 10/993,340

(22) Filed: Nov. 19, 2004

Related U.S. Application Data

(60) Provisional application No. 60/527,934, filed on Dec. 8, 2003.

(51) Int. Cl.
*G01N 33/53* (2006.01)

(52) U.S. Cl. .................... 436/514; 422/56; 422/57; 422/58; 422/61; 422/187; 435/287.1; 435/805; 436/518; 436/524; 436/525; 436/828

(58) Field of Classification Search .............. 422/56, 422/57, 58, 61, 187, 188; 436/514, 518, 436/524, 525, 828; 435/287.1, 805
See application file for complete search history.

(56) References Cited

U.S. PATENT DOCUMENTS

| | | | |
|---|---|---|---|
| 4,540,659 A | 9/1985 | Litman et al. |
| 4,700,714 A | 10/1987 | Fuisz |
| 4,703,017 A | 10/1987 | Campbell et al. |
| 4,743,560 A | 5/1988 | Campbell et al. |
| 4,826,759 A | 5/1989 | Guire et al. |
| 4,999,285 A | 3/1991 | Stiso |
| 5,028,535 A | 7/1991 | Buechler et al. |
| 5,158,869 A | 10/1992 | Pouletty et al. |
| 5,179,005 A | 1/1993 | Phillips et al. |
| 5,229,073 A | 7/1993 | Luo et al. |
| 5,238,652 A | 8/1993 | Sun et al. |
| 5,260,222 A | 11/1993 | Patel et al. |
| 5,266,497 A | 11/1993 | Imai et al. |
| 5,296,347 A | 3/1994 | LaMotte |
| 5,356,782 A | 10/1994 | Moorman et al. |

(Continued)

FOREIGN PATENT DOCUMENTS

EP  0 279 574 A1  8/1988

(Continued)

OTHER PUBLICATIONS

Brady et al., Journal of Food Protection, 56(3):229-233, Mar. 1993.

(Continued)

*Primary Examiner*—Bao-Thuy L Nguyen
(74) *Attorney, Agent, or Firm*—Charm Sciences, Inc.; Richard J. Long

(57) ABSTRACT

Embodiments described herein include methods and assays for detecting an analyte in a sample using a plurality of control zone capture agents. Some embodiments include detection of multiple analytes in a sample utilizing a plurality of analyte binders and a control zone containing multiple control zone capture agents. In some embodiments, the multiple control zone capture agents capture a plurality of binders within one control zone. Test results are determined by comparison of the control zone signal to a test zone signal.

21 Claims, 6 Drawing Sheets

U.S. PATENT DOCUMENTS

| | | |
|---|---|---|
| 5,395,754 A | 3/1995 | Lambotte et al. |
| 5,434,053 A | 7/1995 | Piasio |
| 5,451,504 A | 9/1995 | Fitzpatrick et al. |
| 5,521,102 A | 5/1996 | Boehringer et al. |
| 5,541,059 A | 7/1996 | Chu |
| 5,541,069 A | 7/1996 | Mortensen et al. |
| 5,545,721 A | 8/1996 | Carroll et al. |
| 5,585,241 A | 12/1996 | Lindmo |
| 5,591,645 A | 1/1997 | Rosenstein |
| 5,602,040 A | 2/1997 | May et al. |
| 5,622,871 A | 4/1997 | May et al. |
| 5,656,448 A | 8/1997 | Kang et al. |
| 5,656,502 A | 8/1997 | MacKay et al. |
| 5,712,172 A | 1/1998 | Huang et al. |
| 5,714,389 A | 2/1998 | Charlton et al. |
| 5,726,010 A | 3/1998 | Clark |
| 5,726,013 A | 3/1998 | Clark |
| 5,739,041 A | 4/1998 | Nazareth et al. |
| 5,753,517 A | 5/1998 | Brooks et al. |
| 5,766,962 A | 6/1998 | Childs et al. |
| 5,780,308 A | 7/1998 | Ching et al. |
| 5,874,216 A | 2/1999 | Mapes |
| 5,939,272 A | 8/1999 | Buechler et al. |
| 5,962,339 A | 10/1999 | Midgely |
| 5,985,675 A | 11/1999 | Charm et al. |
| 6,001,658 A | 12/1999 | Fredrickson |
| 6,121,008 A | 9/2000 | Fitzpatrick et al. |
| 6,177,281 B1 | 1/2001 | Manita |
| 6,281,004 B1 | 8/2001 | Bogen et al. |
| 6,319,466 B1 | 11/2001 | Markovsky et al. |
| 6,368,876 B1 | 4/2002 | Huang et al. |
| 6,475,805 B1 | 11/2002 | Charm et al. |
| 6,509,196 B1 | 1/2003 | Brooks et al. |
| 6,528,323 B1 | 3/2003 | Thayer et al. |
| 6,656,744 B2 | 12/2003 | Pronovost et al. |
| 6,699,722 B2 | 3/2004 | Bauer et al. |
| 2003/0049857 A1 | 3/2003 | Chan |
| 2003/0119203 A1 | 6/2003 | Wei et al. |
| 2003/0162236 A1 | 8/2003 | Harris et al. |
| 2003/0199004 A1 | 10/2003 | Fong |
| 2004/0002063 A1 | 1/2004 | Chan et al. |
| 2004/0002165 A1 | 1/2004 | Buchanan et al. |
| 2004/0161859 A1 | 8/2004 | Guo et al. |
| 2004/0171092 A1 | 9/2004 | Harris et al. |
| 2004/0241750 A1 | 12/2004 | Nordman et al. |
| 2004/0241882 A1 | 12/2004 | DiNello et al. |

FOREIGN PATENT DOCUMENTS

| | | |
|---|---|---|
| EP | 0 291 176 B1 | 11/1988 |
| EP | 0 291 194 B1 | 11/1988 |
| EP | 0 299 428 A2 | 1/1989 |
| EP | 0 306 336 B1 | 3/1989 |
| EP | 0 321 145 A2 | 6/1989 |
| EP | 0 378 391 B1 | 7/1990 |
| EP | 0 516 095 A2 | 12/1992 |
| EP | 0 544 413 A1 | 6/1993 |
| EP | 0 582 231 A1 | 2/1994 |
| EP | 0 593 112 B1 | 4/1994 |
| EP | 0 284 232 B1 | 6/1995 |
| WO | WO 90/15327 | 12/1990 |
| WO | WO 91/19980 | 12/1991 |
| WO | WO 92/22797 | 12/1992 |
| WO | WO 93/03175 | 2/1993 |
| WO | WO 94/02850 | 2/1994 |
| WO | WO 94/23300 | 10/1994 |
| WO | WO 96/38720 | 12/1996 |
| WO | WO 96/42017 | 12/1996 |
| WO | WO 97/03209 | 1/1997 |
| WO | WO 97/05287 | 2/1997 |
| WO | WO 02/10708 A2 | 2/2002 |
| WO | WO 2004/109285 A1 | 12/2004 |

OTHER PUBLICATIONS

Charm et al., Journal of the Association of Food and Drug Officials, 58(1), 17-29, Jan. 1994.

Charm et al., J. Assoc. Off. Anal. Chem., 71(2), 1988.

Hassnoot et al., "Evaluation of a Sol Particle Immunoassay (SPIA) Based Single-Strep Test for the Detection of Sulfadimindine Residues," Euro Residue III (1996) 461-465.

"A Short Guide- Developing Immunochromatographic Test Strips," 1996, Lit. No. TB500, Millipore Corporation, Bedford, MA, USA.

Verheijen et al., "Single-Strep Strip Tests for Residue Analyses," DLO-State Institute for Quality Control of Agricultural Products (RIKILT-DLO) (Jun. 3, 1998).

Wong, "Chemistry of Protein Conjugation and Cross-Linking," 39-40, 1991, Boca Raton, Florida.

Wong, "Chemistry of Protein Conjugation and Cross-Linking," 122-123, 1991, Boca Raton, Florida.

Wong, "Chemistry of Protein Conjugation and Cross-Linking," 195-204, 1991, Boca Raton, Florida.

Hermanson et al., "Immobilized Afinity Ligand Techniques," 98-110, 1992, San Diego, California.

Hermanson, "Bioconjugate Techniques," 169-186, 1996, San Diego, California.

METHOD AND ASSAY FOR DETECTION OF RESIDUES

REFERENCE TO PRIOR APPLICATION

This application is based on and claims priority from U.S. Provisional Patent Application Ser. No. 60/527,934, filed Dec. 8, 2003, which is incorporated by reference.

BACKGROUND

Antibiotic residues in foods are a major food safety concern. Health issues include bacterial resistance to drugs and allergic reactions. To avoid the impact of such health issues, food is tested worldwide for antibiotics and other contaminants. One type of test method uses what is commonly known as a lateral flow test strip.

Lateral-flow test strips for detecting one or more analytes in a fluid sample may include a capture agent immobilized within a region of the test sometimes referred to as a detection zone. Detection zones can include test zones and control zones. A typical capture agent has binding affinity for a substance that may be in the mobile phase of the test strip.

Lateral-flow tests in which the binding of a substance from a mobile phase to a capture agent generates a visible signal, that can be interpreted visually or using a reader, such as a spectrophotomer, are well known in the art. Examples of such devices are described in U.S. Pat. No. 5,985,675, issued Nov. 16, 1999; and U.S. Pat. No. 6,319,466, issued Nov. 20, 2001, and U.S. patent application Ser. No. 10/289,089, filed Nov. 6, 2002 (based on U.S. Provisional Application 60/332,877, filed Nov. 6, 2001) all of which are incorporated herein by reference.

Lateral-flow tests are widely used in the food products industry. One application is in testing milk. The United States Food and Drug Administration (FDA) requires that bulk milk tankers be tested for unsafe levels of beta-lactam antibiotics. The sensitivity required pursuant to Appendix N of the Pasteurized Milk Ordinance is: amoxicillin 10 parts per billion ("ppb"), ampicillin 10 ppb, penicillin G 5 ppb, ceftiofur 50 ppb, cephapirin 20 ppb, and cloxacillin 10 ppb (the "safe levels"). The FDA also requires that certain milk tests be automatically (electronically) analyzed and recorded. It is desirable, therefore, to provide milk-testing personnel with a user-friendly test that can be analyzed with or without a reader and can detect multiple beta-lactams, including the six beta-lactams listed above ("the target beta-lactams"), when present at or above the safe level.

SUMMARY

Disclosed herein is a method and apparatus, such as a lateral flow test strip type test, for detection of a contaminant in a sample. Antigens, haptens and their antibodies, hormones, vitamins, drugs, metabolites and their receptors and binding materials, fungicides, herbicides, pesticides, plant, animal and microbial toxins, may be determinable using the present methods and apparatuses. Other analytes that may be determinable by the disclosed methods and apparatuses include antibiotics, such as beta-lactams, cephalosporins, erythromycin, sulfonamides, tetracyclines, nitrofurans, quinolones, vancomycin, gentamicin, amikacin, chloramphenicol, streptomycin and tobramycin and toxins, such as mycotoxins, such as aflatoxin and vomitoxin and drugs of abuse, such as opioids and the like, as well as the metabolites thereof.

The test can include one or multiple binders each with binding affinity for one or more analytes. The test can also include a test zone capture agent and one or more control zone capture agents with binding affinity for the binders. In an example, two control zone capture agents are used each with affinity to a different binder. In another example, two control zone capture agents are used and the two control zone capture agents also have binding affinity to each other.

An example described herein is a test for detection of beta-lactam antibiotics, including test strips sensitive to penicillin G, amoxicillin, ampicillin, ceftiofur, cephapirin and cloxacillin with sensitivity to each at or below safe level. Such a test can include a binder for beta-lactam antibiotics, for example a beta-lactam binding protein derived from Geobacillus stearothermophilus (sometimes referred to as Bacillus stearothermophilus) ("B.st.") with affinity to multiple beta-lactams including the target beta-lactams ("the BL binder"). Generally binders with affinity to multiple drugs are hereinafter referred to as "multianalyte binders".

The test can also include a binder with greater specificity for a particular analyte as compared to a multianalyte binder, hereinafter referred to as a "specific binder", for example an antibody to an antibiotic such as cloxacillin ("cloxacillin binder") to which the multianalyte binder, such as the BL binder, may not have adequate sensitivity. In such a test, a test zone can contain a capture agent for the binder, for example representative antibiotics. When two binders are used, such as a multianalyte binder and a specific binder, a detection zone can include capture agents for both, for example capture agents immobilized in separate test zones. Immobilization can be through use of a carrier protein, such as BSA.

The test can also utilize two or more binders having sensitivity for unrelated analytes such as different families of antibiotics or toxins.

A control zone can be used for comparison to the one or more test zones or as a signal that the test functioned properly and is complete. A control zone can also include a capture agent. In an example, one of the control zone capture agents includes an antibody binding protein such as protein A, protein G or protein AG or recombinant forms of the same. In another example, one of the control zone capture agents includes an antibody, for example an antibody to a multianalyte binder immobilized on the control zone prior to testing. It is also possible that an antibody to a multianalyte beta lactam binder is not immobilized in the control zone and is instead combined with a beta lactam binder prior to testing and flows to the control zone for capture. In such an example, there is a single capture agent immobilized on the control zone prior to testing which can be an antibody binding protein.

When the control zone capture agents include an antibody binding protein, and an antibody, the capture agents may have affinity to each other, and, therefore, if combined, may have binding to each other. The control zone capture agents need not, however, have affinity to each other. For example, the control zone capture agents can include a variety of antibodies, receptors, binding proteins and the like, each with affinity to at least one of the analyte binders. Generally, however, when multiple test zones are employed, it is preferable to have a control zone be used for comparison to more than one test zone. In that way, one control zone can be used to compare to more than one test zone, thereby simplifying test result interpretation. For example, if there are two test zones one control zone can be used, or if there are four test zones then two control zones can be used.

In another aspect, in which one test zone and one control zone are used to capture one labeled binder, the control zone includes multiple capture agents, each with different affinity to a binder, such as each with affinity to different parts of the binder.

DETAILED DESCRIPTION

Figure 1:
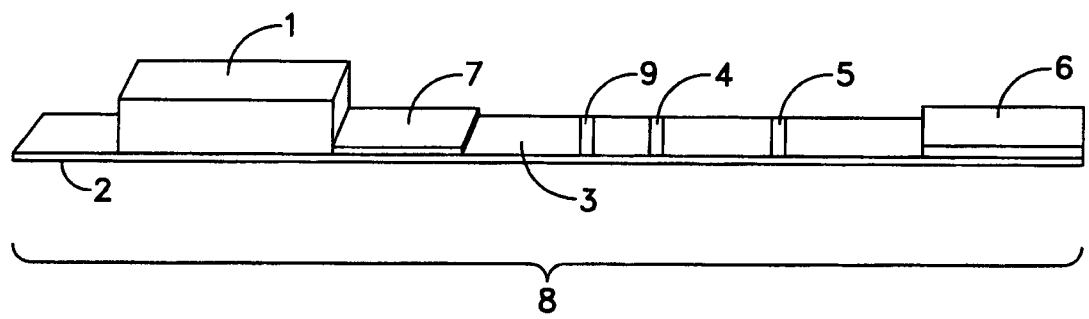
FIG. 1 is a side view of an embodiment having two test zones and a control zone.

An analyte or chemical residue test device and method for detecting an analyte in a sample is described herein. Often a substance such as milk has one or more analytes that need to be detected. To detect an analyte a binder for the analyte can be employed. The binder can be a binding protein such as an enzyme, antibody, receptor or other substance capable of binding to the analyte to form an analyte-binder complex. The binder, or analyte-binder complex, can be detected through various methods including labeling the binder, and, therefore, the resulting complex, with a visible label, such as a gold particle, and capturing the labeled complex with a capture agent.

In embodiments utilizing a lateral flow test strip, the strip can include a solid support, such as nitrocellulose with sufficient pore size to allow liquid to flow along the membrane, and a separate region for applying a fluid sample ("sample pad"). The test strip can include one or a plurality of binders selected for their binding affinity for the analytes to be detected. Binders can be located on the sample pad or elsewhere on the test strip.

In an example of using the test strip, fluid is applied to a sample pad. The sample fluid solubilizes the binders and migrates through the test strip by the forces of lateral capillary flow. The binders bind to analyte in the sample. The fluid flows to a detection zone. The detection zone can include one or more test zones and one or more control zones, each containing capture agents.

In an example, a test zone capture agent can be, for example, an analyte, representative analyte, or analyte analogue. The capture agent at some point must be immobilized to the strip so that it is either removed from sample flow or is not solubilized by sample fluid flow. Immobilization on the strip, so that the capture agent is not solubilized by fluid flow, can be accomplished using a carrier protein such as bovine serum albumin (BSA), or other carrier protein well known in the art, for example ovalbumin (OVA) or keyhole limpet hemocyanin (KLH).

Each test zone capture agent captures all or a portion of the binder, from what is known as the mobile phase, which is not already bound with sample analyte. A binder that is bound by analyte from the sample tends not to be captured at the test zone. Binders that are not captured at the test zone can be captured in the control zone or flow through to a disposal pad.

In an embodiment, a specific binder is a cloxacillin binder and a multianalyte binder is a BL binder. Both the cloxacillin binder and the BL binder can be detectably labeled, for example using gold particles. The labeled cloxacillin binder and labeled beta-lactam binder can be combined in a solution and applied, for example, by spraying, within or proximate to a pretreated POREX® (POREX is a registered trademark of Porex Technologies Corp, Georgia USA) sample pad in contact with a nitrocellulose membrane. The binders can also be combined with the sample in a container, such as a test tube, and added to the test strip with the sample. When exposed to a sample such as fluid milk, the cloxacillin binder binds to cloxacillin in the milk and the BL binder binds to beta-lactams (including to some extent cloxacillin) in the milk to form complexes. Lateral capillary flow carries the complexes, and any uncomplexed labeled binders, to the test zone area of the strip.

In an embodiment using two binders, multiple test zones can be employed to capture the binders in separate zones. In an example in which cloxacillin binder and BL binder are used, the first test zone capture agent can include immobilized cloxacillin and the second test zone capture agent can include an immobilized different beta-lactam, such as ceforanide. In an embodiment in which the positions are reversed, the first test zone capture agent can include a representative beta-lactam and the second test zone capture agent can include cloxacillin. In the test zones, the capture agents can capture the binders that have not been previously bound by sample analyte. Such attachment at the test zone can generate a visible signal when a detectable label, such as gold or other label well known in the art, is used. Other particles that may be useful include, but are not limited to, colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles, colloidal metal ferrite particles, any of the above-mentioned colloidal particles coated with an organic or inorganic layer; protein or peptide molecules; liposomes; or organic polymer latex particles, such as polystyrene latex beads. Other labels may also be useful including, but not limited to, luminescent labels; fluorescent labels; or chemical labels, such as electroactive agents (e.g., ferrocyanide); enzymes; radioactive labels; or radiofrequency labels.

In an embodiment, two control zone capture agents are employed within the same control zone. The capture agents can each capture a different binder. In an embodiment in which a cloxacillin binder and a BL binder are both employed, protein A can be one control zone capture agent and an antibody to beta-lactam binder ("anti-BL binder") can be the other capture agent. In embodiments in which the anti-BL binder also has protein A binding affinity, such as when the anti-BL binder is rabbit antibody, the two control zone capture agents may become linked. In addition, either or both the protein A and anti-BL binder can be immobilized on the control zone using a carrier protein such as BSA.

In another embodiment, one control zone capture agent can be attached at the control zone and another control zone capture agent can be applied later for example by flowing to the control zone with the sample. For example, when the binders are a cloxacillin binder and a BL binder, the control zone can include protein A and anti-BL binder. Alternatively, the control zone can include protein A and the anti-BL binder can be bound to the BL binder and added to the strip with the BL binder such as on the sample pad. BL binder will retain beta-lactam binding activity after binding to anti-BL binder, but not after binding to a beta-lactam drug in the sample. In such an embodiment, the control zone capture agent is selected for its affinity to the anti-BL binder at a site not occupied by BL binder. Examples of such capture agents include Protein A, protein G, recombinant protein AG or other substances such as substances that bind, for example, to the constant region of an antibody.

In an embodiment, detectably labeled multianalyte binder ("labeled multianalyte binder) and detectably labeled specific binder ("labeled specific binder") are combined with unlabeled binders, such as unlabeled antibodies. The unlabeled antibodies are selected for their affinity to antibiotics to which the other binders, for example the multianalyte binder, are oversensitive. Such unlabeled binders compete with labeled multianalyte binders for a specific antibiotic and, thereby, reduce test sensitivity to the antibiotic/analyte to which the unlabeled binders have affinity. The unlabeled binders can have affinity for some or all of the analyte to which the labeled multianalyte binder has affinity. By including unlabeled binders with affinity for some, but not all, of the analytes to which a competing labeled binder has affinity, sensitivity of the test to those selected antibiotics/analytes will be reduced.

In some embodiments there is excess capture reagent in the control zone. Excess capture reagent will provide consistent control zone detection. In other control zone embodiments there is an excess of the general antibody binder, such as protein A, relative to the multianalyte binder capture agent, such as anti-BL binder, such as rabbit antireceptor. In a particular example using protein A and rabbit anti-BL binder, the control zone will have sufficient excess protein A available for capturing cloxacillin binder and binding the anti-BL binder.

In certain embodiments, in a negative sample the control zone will capture fewer labels as compared to any one of the test zones, in a positive sample for a single analyte or family, the control zone will capture more labels than one of the test zones and fewer labels than the other and, if positive for all analytes, each of the test zones will capture fewer labels as compared to the control zone.

Including multiple capture agents at the control zone, such as both protein A, or other general antibody binder, and specific antibody to a binder, such as anti-BL binder, provides the possibility of a test strip for detection of multiple analytes such as multiple antibiotics. For example, a test strip to detect sulfonamides, tetracyclines, amphenicols or macrolides, possibly combined on a test strip to detect beta-lactams, with a single control zone for comparison to multiple test zones for the different antibiotics. A control zone can have multiple specific antibodies to particular binders, multiple multianalyte binder antibodies, multiple antibody binding proteins or combinations thereof. Similarly, the control zone can include multiple antibodies of different host species and not necessarily include a general antibody binder. For example, if one binder is a mouse monoclonal antibody and another is a rabbit polyclonal antibody, the control zone can include an anti-mouse antibody and an anti-rabbit antibody.

In another embodiment, the assay can be in the form of a so-called sandwich assay using different types of binders, such as a combination of polyclonal and monoclonal antibodies or a combination of different species polyclonal antibodies. Tests to detect multiple analytes using a sandwich assay can include a plurality of labeled analyte binders that bind with different analytes. The test zone can include multiple immobilized binders for the analyte, for example with affinity to different regions of the analyte to which the labeled antibody has affinity. The control zone could include a combination of immobilized capture agents including, for example, combinations of anti-species antibodies for reactions to each of the different analyte binders. The control zone could also combine, depending on the binders used, a combination of general antibody binding protein, such as protein A, and an antibody for one of the binders to which protein A does not have adequate affinity, such as anti-mouse antibody. In such an embodiment, as with the other embodiments described herein in which the non-sandwich format is used, either the analyte binder can be labeled with a visible label or, in an embodiment, the label can require a further reaction such as when the label is an enzyme or substrate of an enzyme linked immunosorbent assay (ELISA).

In another embodiment, one type of binder, for example a labeled polyclonal antibody, can be used to detect a single analyte or a group of related analytes. One test zone and one control zone can be used to capture the labeled binder. The control zone can include multiple capture agents, each with different affinity to the binder, such as each with affinity to different parts of the binder. For example, if the labeled antibody is a rabbit polyclonal, the control zone capture agents can include, for example, an anti-rabbit antibody and an antibody binding protein such as protein A. By including different control zone capture agents, it may be possible to improve binder capture at the control zone and, thereby, improve the control zone signal.

In some embodiments BL binder is isolated directly from, for example, B.st., by immobilized ligand affinity chromatography techniques that are well known in the art.

The binder can also be expressed from other hosts by inserting into the host genome the sequence of the BL binder from B.st.

Another example of a useful multianalyte binder, that can be used in certain embodiments, includes a beta-lactam binding protein isolated from *Bacillus lichenformis*. Other possibly useful binders include macromolecules, such as monoclonal or polyclonal antibodies, hormone receptors and enzymes and synthetic receptors such as those generated through molecular imprinting of synthetic polymers or molecular imprinting inside dendrimers.

EXAMPLES

One embodiment includes a three-zone test for detection of penicillin-G, amoxicillin, ampicillin, cloxacillin, ceftiofur and cephapirin at safe level. This embodiment includes two test zones and one control zone. The first test zone solution includes a cloxacillin-BSA conjugate at 0.1-2 mg/ml, buffered with 10 millimolar (mM) sodium phosphate, pH 5.5-7.0, containing 20% sucrose. The mixture was sprayed 1.6 cm above the bottom edge of a nitrocellulose membrane at a rate of 0.6 μl/cm. The second test zone solution includes a ceforanide-BSA conjugate at 0.55-0.8 mg/ml in 10 mM sodium phosphate, pH 6.9, containing 15% sucrose sprayed onto nitrocellulose using a BIODOT® sprayer. The second test zone was sprayed 2.2 cm above the bottom edge of the nitrocellulose at a rate of 0.8 μl/L.

The ceforanide-BSA conjugate, was made by using the amino group on the ceforanide to add a sulfhydryl group. Next a cross-linking agent, for example, Sulfosuccinimidyl-4-(N-maleimidomethyl)cyclohexane-1-carboxylate (sulfo-SMCC), was added to link the sulfhydryl group on the ceforanide derivative to the amino group on the carrier protein.

The cloxacillin-BSA conjugate was made by activating the carboxyl group of cloxacillin with a carbodiimide and N-hydroxysulfosuccinimide (S-NHS) and subsequently binding the cloxacillin activated compound to amino groups on BSA. Cloxacillin (1 g) is dissolved in dry DMSO. The S-NHS was dissolved in dry DMSO and added to the cloxacillin solution. To this solution (approximately 30 ml), 0.5 ml of diisolpropyl carbodiimide was immediately added and the reaction allowed to proceed for 2 to 3 hours. The reaction was then extracted 3 times with dry petroleum ether and the DMSO portion was retained. The activated cloxacillin in DMSO was gradually added to a solution of BSA (4-g/70 ml) in 0.02 M sodium phosphate buffer at pH 7.2. This reaction was allowed to proceed overnight with mixing. The resulting cloxacillin-BSA conjugate was desalted to remove free cloxacillin.

In an alternative method for making the cloxacillin-BSA conjugate, dissolve 1 gram of sulfhydryl blocked BSA in 9 ml of 0.1 M potassium carbonate buffer at pH 10.0. While stirring add dropwise a cloxacillin solution (100 mg/ml in DMSO) to the BSA solution. Place in a 15 ml centrifuge tube and mix overnight in an orbital shaker. Neutralize the solution by adding 4.0 ml of 0.4 M phosphate buffer, pH 6.3. Desalt the reaction on FPLC using one high prep 26/10 desalting column equilibrated with 0.02 M phosphate buffer, pH 7.2. To give a theoretical substitution of moles of cloxacillin per mole of BSA of 5.0, 32.5 mg of cloxacillin or 0.325 ml is added to the BSA solution.

In this embodiment the gold label includes a combination of BL binder gold conjugate and monoclonal cloxacillin antibody (cloxacillin binder) gold conjugate. Approximately 30% of the solution includes gold coated with 600 U (units) of beta-lactam binder (one unit is defined as the amount of purified antibiotic binder able to bind 1000 counts per minute of radiolabeled antibiotic, such as when using the Charm II System) purified from B.st. and approximately 20% consists of gold coated with 1000 U of purified cloxacillin binder. To the remainder of the solution was added a 10 mM sodium phosphate buffer, pH 7.4, containing 40% sucrose and 10% BSA. The combined bead solution was sprayed at 0.7 to 0.9 µl/cm with 2 to 4 passes onto POREX®.

The monoclonal antibody to cloxacillin was purified by ammonium sulfate precipitation at 50% saturation and dialyzed against 20 mM sodium phosphate buffer, pH 7.2, containing 50 mM sodium chloride and then purified using a protein A column.

The BL binder was purified by passing a solubilized receptor solution through a column containing a bound beta-lactam ligand possessing beta-lactam binding activity. As the impure receptor solution was passed through the column, the receptor was bound to the beta-lactam and retained on the column. The column was washed to further remove impurities and then an elution solution was used, containing hydroxyl/amine, to breaks the bond between the receptor and the beta-lactam allowing the receptor to be eluted from the column.

The control zone was made as follows:

a) Preparation of BSA-Protein A Conjugate 1) 8 bottles of 5 mg recombinant protein A was dissolved in about 12 ml of 0.16 M borate buffer, pH 8.1. Next, 13 mg S-SMCC was weighed out and dissolved in 1 ml of DMSO. A 30 µl portion of the S-SMCC solution was added to the protein A solution and mixed for 1 hour. 500 mg BSA was then dissolved in 8 ml of 0.4 M phosphate buffer, pH 6.3. The Protein A and BSA solutions were mixed together and brought to pH 7.0 with additional 0.4 M phosphate buffer. The solution was then brought to 30 ml with water.

b) Preparation of Rabbit Anti-Receptor Antibody.

The antibody was made in rabbits using purified beta-lactam receptor from Geobacillus stearothermophilus as the immunogen. The rabbit anti-receptor antibody was purified on a protein A column and diluted to 5 mg/ml protein for storage.

c) Application to Test Strip

BSA-Protein A conjugate prepared as described above was diluted 25 fold in 10 mM phosphate buffer, pH 6.95, containing 5% sucrose. Rabbit anti-receptor was prepared as described above and diluted 150 times in 10 mM phosphate buffer, pH 6.95, containing 25% sucrose. The two dilute solutions were then combined and immobilized onto the nitrocellulose on the control zone by spraying the solution onto the control zone.

With reference to FIG. 1 and the above specific example, the sample application area 7 includes the cloxacillin binder gold conjugate and the BL binder gold conjugate. Test zone 9 can include the immobilized cloxacillin-BSA conjugate and test zone 4 can include the immobilized ceforanide-BSA conjugate. The control zone 5 could, therefore, include the BSA-protein A conjugate and rabbit anti-receptor antibody.

DETAILED DESCRIPTION OF THE DRAWINGS

FIG. 1 shows the test strip apparatus 8, comprised of nitrocellulose membrane 3 and a binder application area 7 onto which the labeled binders can be added. The binder application area can be, for example, POREX® attached to solid support 2. If a sample pad 1 is used, sample is contacted to sample pad 1. Alternatively, sample can be applied directly to the binder application area 7. If a sample pad 7 is used, sample flows from sample pad 1 to the sample application area 7 containing, in an example, labeled specific binder and labeled multianalyte binder. Labeled specific binder and labeled multianalyte binder will bind analyte from the sample and flow along the nitrocellulose membrane 3 to test zone 9 and test zone 4. A portion of labeled specific binder and labeled multianalyte binder, unbound by sample analyte, will be captured at the related test zone. Remaining labeled binder, whether or not bound by sample analyte, will flow to, and can bind to, control zone 5. Some labeled binder may also flow past the control zone and into the disposal pad 6. A stronger signal in the control zone as compared to the test zone is a positive result. A weaker signal in the control zone as compared to the test zone is a negative result.

Figure 2:
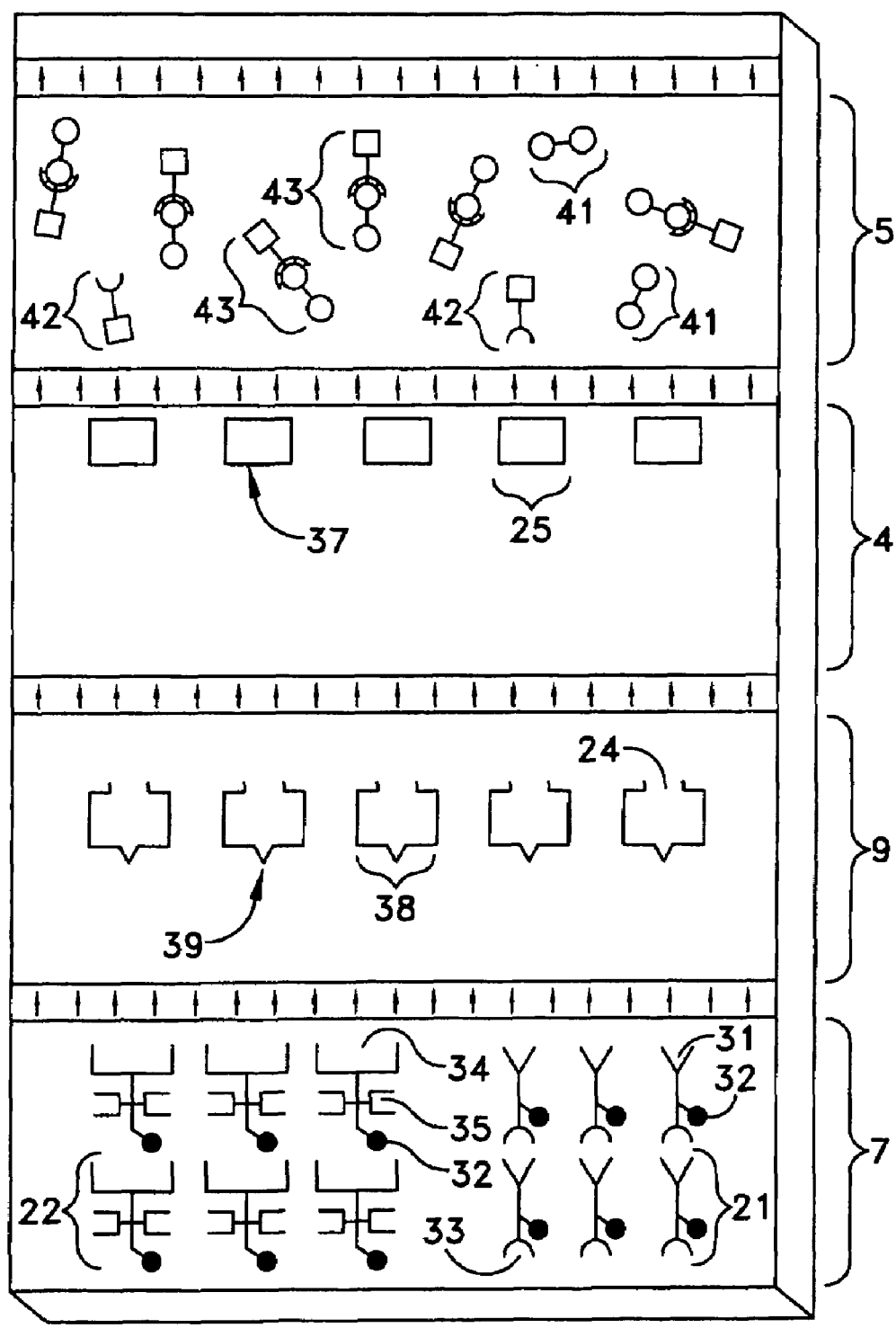
FIG. 2 is a schematic view of the arrangement of test components on the test strip prior to application of sample.

FIG. 2 shows the test strip components prior to application of sample solution. The arrows indicate the direction of sample flow from the binder application area 7. Not shown is a sample pad 1 or other test solution application area that may precede the binder application area 7. The binders in the application area are, in this example, labeled specific binder 21, in this example labeled cloxacillin binder, and labeled multianalyte binder 22, in this example labeled BL binder. The cloxacillin binder 21 includes cloxacillin binding site 31, detectable label 32, for example gold particle, and protein A binding site 33. The BL binder 22 includes beta-lactam binding site 34, anti-BL binder binding site 35 and label 32. The test zone 9 includes immobilized cloxacillin 38. In this embodiment, the beta-lactam ring of the immobilized cloxacillin is opened, depicted in this drawing as a break 24 in the ring, to reduce or eliminate the affinity of the beta-lactam binding site 34 of the BL binder 22. Binding site 39 on immobilized cloxacillin 38 is available to capture specific binder 21 unbound by cloxacillin from the sample. The test zone 4 includes immobilized representative beta-lactam 25 such as ceforanide. BL binder binding site 37 is available to capture BL binder 22 unbound by beta-lactam from the sample. The control zone 5 includes protein A 41. The control zone 5 also includes anti-BL binder 42. Protein A can capture cloxacillin binder 21 through attachment to the protein A site 33. As a result, protein A can capture both bound and unbound cloxacillin binder. If mixed together, Protein A 41 can also bind to anti-BL binder 42 at the control zone 5 to form an anti-BL binder-protein A complex 43 that may retain the ability to capture both cloxacillin binder 21 and BL binder 22. Anti-BL binder 42 can capture BL binder 22 unbound by beta-lactam from the sample or BL binder 22 bound by beta-lactam from the sample.

Figure 3:
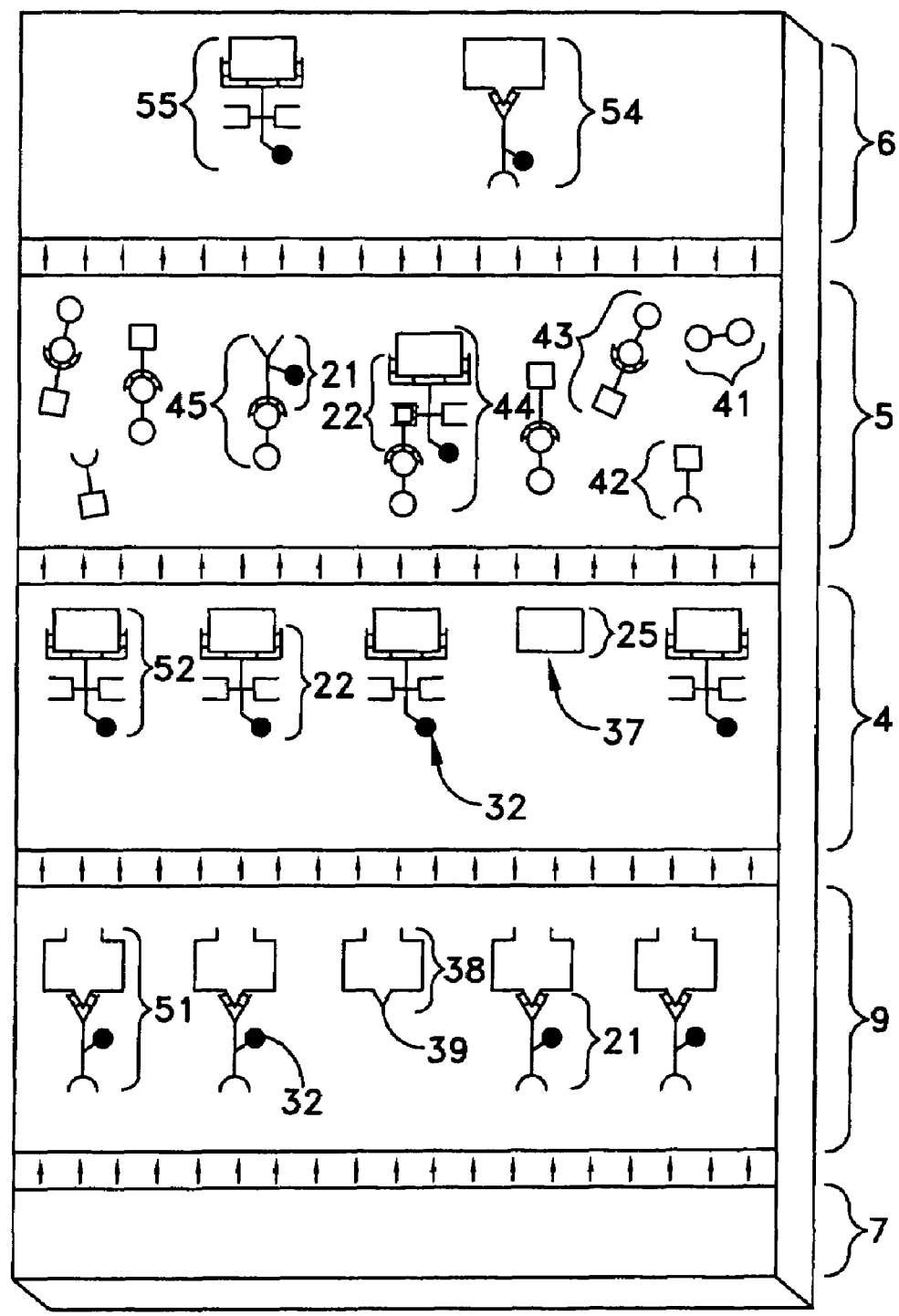
FIG. 3 is a schematic view of the test components after application of sample. The movement of fluid and formation of complexes is shown in an example of a test that is negative for both cloxacillin specifically and beta-lactams.

FIG. 3 shows a sample that is negative for both beta-lactams generally and the specific beta-lactam cloxacillin at the appropriate level of detection. After application of the sample, test components flow out of binder application area 7. Cloxacillin binder 21, unbound by cloxacillin from the sample, can be captured by cloxacillin immobilized on the first test zone 9 to form a complex 51 that can be detected. Similarly, BL binder 22, unbound by beta-lactam from the test sample, can be captured by beta-lactam 25 immobilized on the second test zone 4 to form complex 52 that can be detected. Protein A 41 in control zone 5, whether complexed to anti-BL binder or alone, can capture both bound and unbound cloxacillin binder 21 that flow past the test zone 9 without being captured. In this figure complex 45 includes cloxacillin binder unbound by cloxacillin from the sample and captured at the control zone. The anti-BL binder 42, whether complexed to protein A, or alone, can capture both bound or unbound BL binder that flow past the test zone 4 without being captured, for example to form complex 44 in the control zone 5. In this figure some sample beta-lactam-BL binder complex 55 and sample cloxacillin-cloxacillin binder complex 54 are not captured and instead flow to the disposal pad 6. Not all labeled binder, whether or not bound by analyte from the sample, is necessarily captured at the test zones or control zone. Remaining label can flow to the disposal zone 6. The negative result can be determined, in the drawing, by counting the labels 32 in the control zone and test zones. In this example, the control zone 5 has two labels. The test zone 4 has four labels and the test zone 9 has four labels. Since the control zone has fewer labels than either of the test zones the test is negative for both cloxacillin and other beta-lactams. Although one beta-lactam from the sample was captured by BL binder 22 to form a complex that was captured 44 at the control zone 5, and one each of BL-binder and cloxacillin binder were bound by antibiotic to form complex 55 and complex 54 respectively, that flowed to the disposal zone 6, the semi-quantitative nature of the test is reflected in the negative result.

Figure 4:
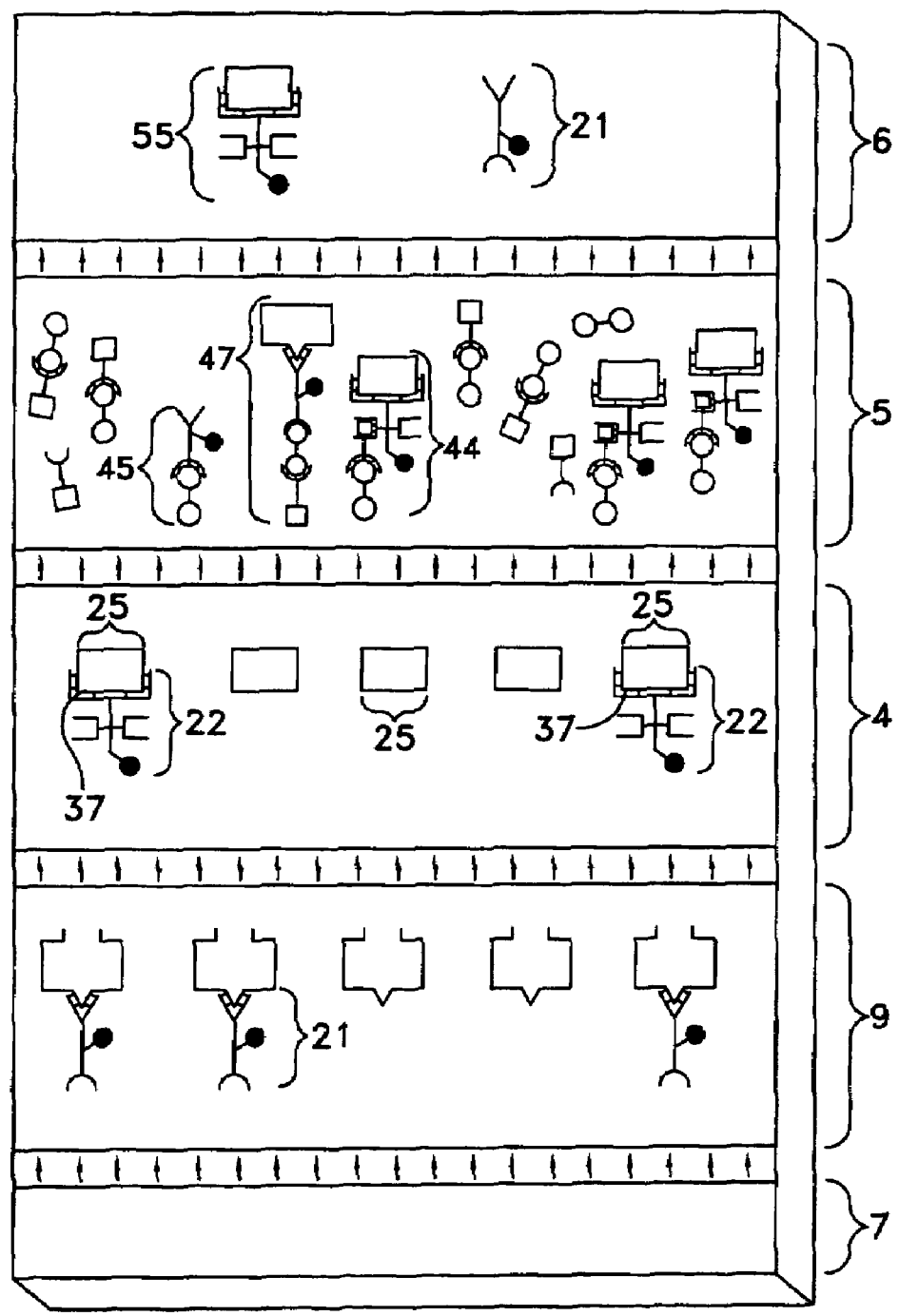
FIG. 4 is a schematic view of the test components after application of sample. Movement of fluid and formation of complexes is shown in an example of a test that is positive for both cloxacillin specifically and beta-lactams.

FIG. 4 shows a test that is positive for both cloxacillin specifically and beta-lactams. Three cloxacillin binders 21 are bound at test zone 9, two BL binders 22 are bound at test zone 4 and five binders are bound at control zone 5. Control zone 5 includes captured BL binder-label-sample beta-lactam complex 44, captured sample cloxacillin binder-label-cloxacillin complex 47 and captured unbound labeled cloxacillin binder complex 45. Disposal zone 6 includes cloxacillin binder 21 and BL binder-sample beta lactam complex 55, both of which slipped through uncaptured.

Figure 5:
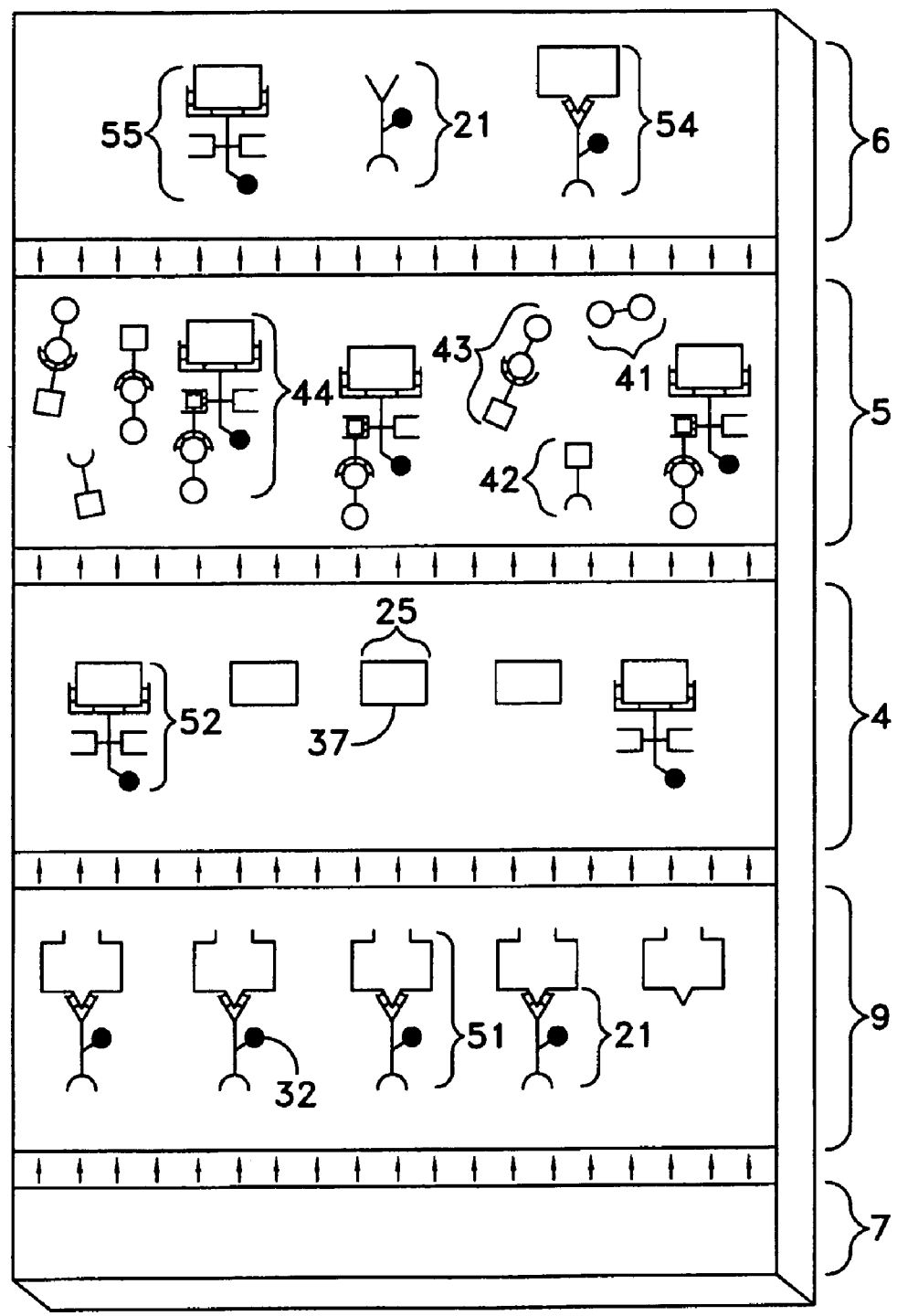
FIG. 5 is a schematic view of the test components after application of sample. Movement of fluid and formation of complexes is shown in an example of a test that is negative for cloxacillin specifically and positive for beta-lactams.

FIG. 5 shows a test that is positive for beta-lactams and negative for cloxacillin specifically. Three labels are captured at the control zone 5 and two labels are captured at test zone 4 while four labels are captured at test zone 9. Three labels are not captured and flow to the disposal zone 6.

Figure 6:
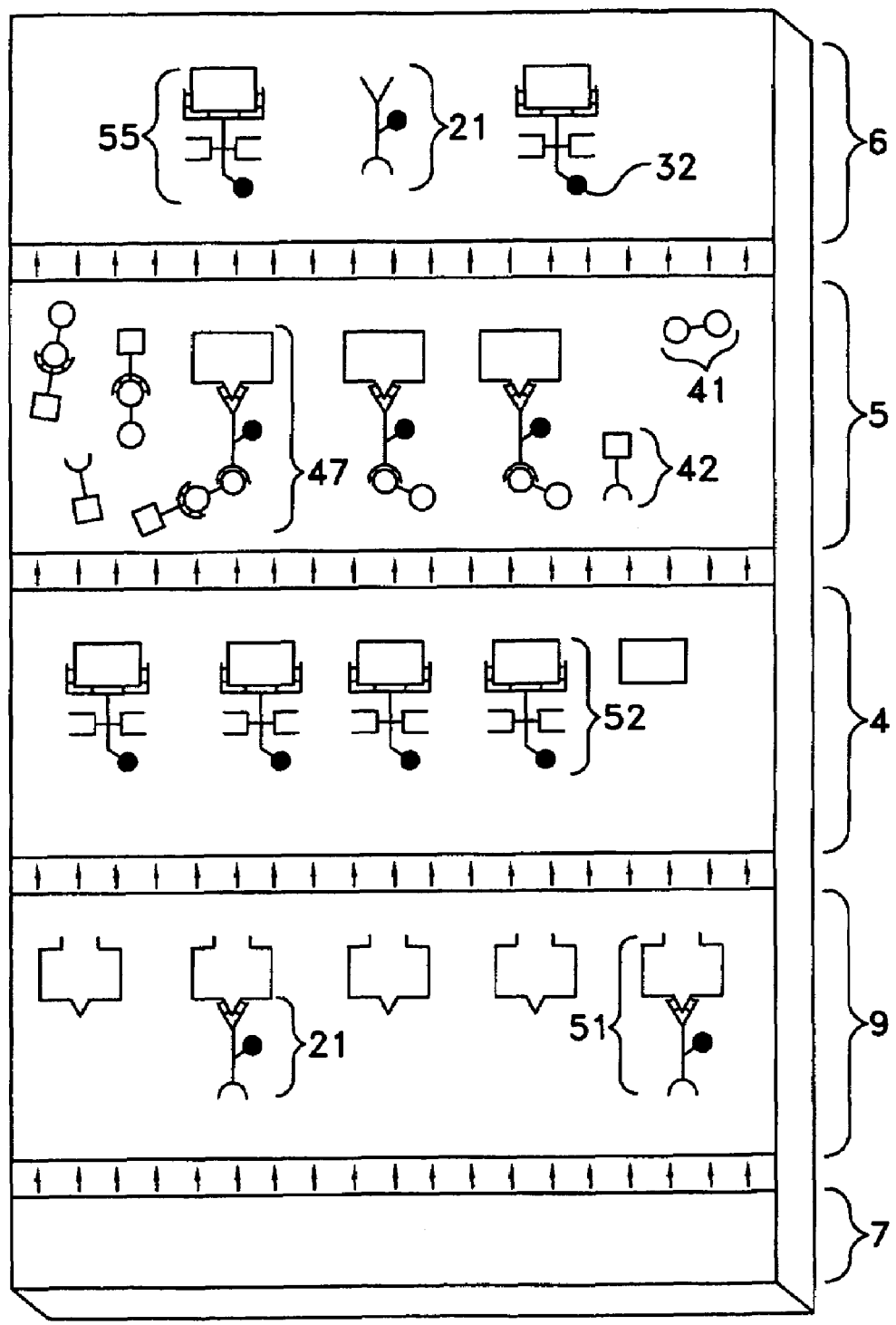
FIG. 6 is a schematic view of the test components after application of sample. Movement of fluid and formation of complexes is shown in an example of a test that is positive for cloxacillin specifically and negative for beta-lactams.

FIG. 6 shows a test that is negative for beta-lactams and positive for cloxacillin specifically. Two labels are captured at the test zone 9 and four labels are captured at the test zone 4 as compared to three labels captured at the control zone 5. Three labels are not captured and flow to the disposal zone 6.

It should be noted that the figures, particularly FIGS. 2-6, are highly simplified depictions designed to exemplify both the various mechanisms of capture, binding and affinity and test result interpretation. Although in these figures the mechanisms are largely described relative to detection of beta-lactams, including cloxacillin, the methods and assays described herein are not so limited.

The invention claimed is:

1. A lateral flow device for detecting a plurality of analytes in a test solution, the test solution including a sample and more than one binder, the binder configured for generating a detectable signal and capable of combining with an analyte present in the sample to form a binder-analyte complex, the device comprising:
   a test strip configured to allow the test solution to flow, the test strip comprising:
   (i) more than one test zone, each test zone having immobilized thereon a test zone capture agent that can capture at least one of the binders that has not formed a binder-analyte complex; and
   (ii) a single control zone having a plurality of control zone capture agents combined together within the control zone, each of the plurality of control zone capture agents having different binding affinities for the binders and each able to capture at least one of the binders, whether or not the binder has formed a binder-analyte complex,
   wherein capture of any of the binders at any of the test zones and the control zone results in a detectable signal and wherein a greater signal in the control zone as compared to any one of the test zones indicates a positive result.

2. The device of claim 1 wherein the control zone capture agents have binding affinity to each other.

3. The device of claim 1 wherein at least one of the control zone capture agents comprises an antibody and another of the control zone capture agents comprises an antibody binding protein.

4. The device of claim 1 wherein at least one of the binders comprises a labeled multianalyte binder disposed on the test strip.

5. The device of claim 4 wherein the multianalyte binder comprises a labeled beta-lactam binder.

6. The device of claim 1 further comprising a labeled specific binder disposed on the test strip.

7. The device of claim 6 wherein the labeled specific binder comprises a labeled cloxicillin binder.

8. The device of claim 1 wherein at least one of the control zone capture agents comprises an anti-beta-lactam binder.

9. The device of claim 1 further comprising at least one unlabeled binder disposed on the test strip wherein the unlabeled binder reduces test sensitivity relative to the analyte to which the unlabeled binder has affinity.

10. The device of claim 1 wherein at least two of the control zone capture agents are antibodies.

11. The device of claim 1 wherein at least one of the control zone capture agents comprises an antispecies antibody.

12. The device of claim 1 wherein at least one of the control zone capture agents comprises an antibody binding protein.

13. The device of claim 12 wherein the antibody binding protein comprises protein A.

14. The device of claim 1 wherein at least one of the control zone capture agents is immobilized on the control zone through attachment to a carrier protein.

15. The device of claim 1 wherein the carrier protein comprises bovine serum albumin.

16. The device of claim 1 wherein one of the plurality of control zone capture agents comprises an antibody binding protein and another of the plurality of control zone capture agents comprises an antibody to which the antibody binding protein has affinity, and wherein the antibody is applied to the test strip with the binders, and flows, either with the binders or attached to one or more of the binders, to the control zone.

17. The device of claim 1 wherein one of the binders comprises a labeled beta-lactam binder and wherein one of the control zone capture agents comprises an anti-beta lactam binder.

18. The device of claim 1 wherein one of the control zone capture agents comprises a polyclonal antibody and another comprises a monoclonal antibody.

19. The device of claim 1 wherein each of the binders comprises an antibody from a different species of animal and at least one of the control zone capture agents comprises an antibody to one of those different species.

20. The device of claim 1 wherein the test solution further comprises additional reagents that are reconstituted when the sample is added to the test strip.

21. The device of claim 1 comprising two binders disposed on the test strip wherein one of the binders comprises a labeled beta lactam binder and the other of the two binders comprises a labeled cloxicillin binder.

* * * * *